United States Patent
Wang et al.

(10) Patent No.: US 11,208,672 B2
(45) Date of Patent: Dec. 28, 2021

(54) METHOD FOR ENZYMATIC DEACIDIFICATION OF POLYUNSATURATED FATTY ACID-RICH OIL

(71) Applicant: SOUTH CHINA UNIVERSITY OF TECHNOLOGY, Guangzhou (CN)

(72) Inventors: Yonghua Wang, Guangzhou (CN); Daoming Li, Guangzhou (CN); Weifei Wang, Guangzhou (CN); Nan Liu, Guangzhou (CN); Bo Yang, Guangzhou (CN); Dongming Lan, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 114 days.

(21) Appl. No.: 16/492,141

(22) PCT Filed: Nov. 15, 2017

(86) PCT No.: PCT/CN2017/111105
§ 371 (c)(1),
(2) Date: Sep. 8, 2019

(87) PCT Pub. No.: WO2018/161631
PCT Pub. Date: Sep. 13, 2018

(65) Prior Publication Data
US 2021/0130860 A1 May 6, 2021

(30) Foreign Application Priority Data
Mar. 9, 2017 (CN) .......................... 201710138652.5

(51) Int. Cl.
*C12P 7/64* (2006.01)
*C12N 11/08* (2020.01)
*C12N 11/089* (2020.01)

(52) U.S. Cl.
CPC .......... *C12P 7/6472* (2013.01); *C12N 11/089* (2020.01); *C12P 7/6454* (2013.01); *C12Y 301/01003* (2013.01)

(58) Field of Classification Search
None
See application file for complete search history.

(56) References Cited

U.S. PATENT DOCUMENTS

2003/0158385 A1  8/2003 Kaczvinsky et al.

FOREIGN PATENT DOCUMENTS

CN  103627685  3/2014
CN  106906194  6/2017

OTHER PUBLICATIONS

Guo et al. FEBS J. Dec. 2015;282(23):4538-47. Epub Oct. 1, 2015. (Year: 2015).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Guo et al "Structure of product-bound SMG1 lipase: active site gating implications" FEBS J Dec. 2015;282(23):4538-47. doi: 10.1111/febs.13513. Epub Oct. 1, 2015.
Li et al "A Novel Process for the Synthesis of Highly Pure n-3 Polyunsaturated Fatty Acid (PUFA)-Enriched Triglycerides by Combined Transesterification and Ethanolysis" J. Agric. Food Chem. 2016, 64, 34, 6533-6538 Publication Date:Aug. 19, 2016 https://doi.org/10.1021/acs.jafc.6b02675.
Li et al "Diacylglycerol production by genetically modified lipase fromMalassezia globosa", Journal of Molecular Catalysis B: Enzymatic vol. 133, Supplement 1, Nov. 2016, pp. S204-S212 https://doi.org/10.1016/j.molcatb.2017.01.006.
Liu et al "Molecular basis for substrate selectivity of a mono- and diacylglycerol lipase from Malassezia globosa", Biochem Biophys Res Commun. Jul. 27, 2012;424(2):285-9. doi: 10.1016/j.bbrc.2012.06.108. Epub Jun. 27, 2012.
Xu et al "Crystal structure of mono- and diacylglycerol lipase from Malassezia globosa", Full wwPDB X-ray Structure Validation Report Deposited on : Nov. 28, 2011.
Xu et al "Crystal structure of SMG1 F278N mutant", Full wwPDB X-ray Structure Validation Report Deposited on : May 12, 2015.

(Continued)

*Primary Examiner* — Christian L Fronda
(74) *Attorney, Agent, or Firm* — JMB Davis Ben-David

(57) ABSTRACT

An enzymatic deacidification method for partial glyceride lipase and PUFA-rich oil, comprising the following steps: 1) mixing a polyunsaturated fatty acid (PUFA)-rich oil with a non-polar organic solvent and a short-chain monohydric alcohol, adding an immobilized partial glyceride lipase to carry out an esterification reaction, wherein the partial glyceride lipase is a mutant obtained by mutating the Phe at the 278th position of Lipase SMG1 as Asn; 2) recovering the immobilized enzyme, and recovering the organic solvent and the monohydric alcohol so as to obtain a deacidified PUFA-rich oil. The partial glyceride lipase does not catalyze alcoholysis of triglyceride and like side reactions, has high deacidification efficiency, low reaction temperature, prevents high temperature oxidation of PUFAs, and the immobilized enzyme may be recovered and reused repeatedly, and thus the present invention has good application prospects in industry.

6 Claims, No Drawings
Specification includes a Sequence Listing.

(56) References Cited

OTHER PUBLICATIONS

Li et al "Preparation of Highly Pure n-3 PUFA-Enriched Triacylglycerols by Two-Step Enzymatic Reactions Combined with Molecular Distillation", Journal of the American Oil Chemists' Society 94(2):1-9 DOI:10.1007/s11746-016-2928-0.

Li et al "Simplified Enzymatic Upgrading of High-Acid Rice Bran Oil Using Ethanol as a Novel Acyl Acceptor", Journal of Agricultural and Food Chemistry 64(35) DOI:10.1021/acs.jafc.6b02518.

* cited by examiner

METHOD FOR ENZYMATIC DEACIDIFICATION OF POLYUNSATURATED FATTY ACID-RICH OIL

CROSS-REFERENCE TO RELATED APPLICATIONS

This is the U.S. National Stage of International Patent Application No. PCT/CN2017/111105 filed Nov. 15, 2017, which was published in Chinese under PCT Article 21(2), and which in turn claims the benefit of Chinese Patent Application No. 201710138652.5 filed on Mar. 9, 2017.

FIELD OF THE INVENTION

The present invention relates to a partial glyceride lipase and a method for enzymatic deacidification of PUFA-rich lipid.

BACKGROUND

Natural animal and vegetable lipids that have not been refined contain a certain amount of free fatty acids, and only by removing the free fatty acids can the lipid reach the standards for storage, processing, food, etc. Therefore, deacidification of lipids is an indispensable procedure in lipid processing.

The method for deacidification of lipid includes chemical deacidification (alkali refining and deacidification), physical deacidification, enzymatic deacidification, etc. Among them, physical deacidification has to be carried out at a higher temperature (generally above 200° C.), where PUFA-rich lipids are prone to oxidation and conversion, so physical deacidification is not suitable for deacidification of PUFA-rich lipid; chemical deacidification is carried out by using the principle of neutralization between alkali and free fatty acids in lipid, however, the yield of the deacidified lipid is low since the soap formed by the neutralization of fatty acid and alkali carries a large amount of neutral lipid, which makes it especially not suitable for deacidification of lipids with high free fatty acid content. Also, in the subsequent process of chemical deacidification, a large amount of industrial wastewater will be generated, which will cause great pollution to the environment, so people have paid less and less attention to the method. Enzymatic deacidification has the characteristics of mild reaction conditions, high catalytic efficiency, high specificity and environmental friendliness. Recycling by enzyme can greatly reduce the cost, thereby having a huge application potential. CN105802730A discloses a method for enzymatic deacidification of rice bran oil, which uses glycerol as an acyl acceptor, and utilizes the high efficiency and specificity of the enzymatic reaction to perform esterification and deacidification under vacuum, wherein after 6 h of reaction, the acid value of rice bran oil decreases from 26.8 mgKOH/g to 1.96 mgKOH/g, and the removal rate of fatty acid reaches 92.69%. CN105419937A discloses a method for enzymatic deacidification of wheat germ oil, which uses an immobilized lipase Novozym 435. After 5 h of reaction at 70° C., the acid value of wheat germ oil decreases from 21.72 mgKOH/g to 2.98 mgKOH/g, and the removal rate of fatty acid reach 86.28%. CN105349259A discloses a process for enzymatic deacidification of high acid value vegetable oil, wherein an immobilized lipase is used to catalyze amidation of free fatty acids and monoethanolamine at a vacuum of 0.075-0.1 MPa with a high reaction selectivity and high catalytic efficiency, wherein problems such as increasing by-products and consumption of neutral oil caused by the enzymatic esterification reaction are avoided. CN101824364A discloses a method for enzymatic refined deacidification of high acid value fish oil, which uses anhydrous ethanol as a acyl acceptor and Novozym 435 as a catalyst. After 1 h of reaction at 50° C., the acid value of tuna oil decreases from 36.3 mgKOH/g to 4.7 mgKOH/g, and the removal rate of fatty acid reach 87.05%. In summary, since enzymatic deacidification has advantages such as mild reaction conditions, high catalytic efficiency, high specificity and environmental friendly process, it is especially suitable for the deacidification of PUFA-rich lipid.

However, the existing enzymatic deacidification techniques generally use a lipase (triglyceride lipase) as a catalyst. Since lipase can also catalyze the reaction of triglycerides and hydroxyl donors, which may cause a large number of side reactions to occur, the yield of deacidified lipids, especially triglycerides in the product, is reduced. Partial glyceride lipase is a special lipase, which has high substrate specificity for partial glycerides (monoglycerides and diglycerides) and may not act on triglycerides. Studies have shown that partial glycerides can be used to synthesize diglycerides (Journal of Molecular Catalysis B: Enzymatic, 2012, 77: 87-91), and can also be used to remove partial glycerides from glyceride mixtures to prepare high purity triglyceride products (Molecules, 2013, 18: 9704-9716).

Further studies have shown that by using the substrate specificity of partial glyceride lipase, the reaction of free fatty acids in PUFA-rich lipids with short-chain monols can be catalyzed to form fatty acid esters, and deacidified lipid with low acid value can be obtained after separation and purification. However, the existing partial glyceride lipases (Lipase SMG1 and Lipase G "Amano" 50) have low catalytic efficiency for long-chain polyunsaturated fatty acids, especially EPA and DHA, resulting in poor deacidification effect as well as a high fatty acid content in the product after being applied for deacidification of PUFA-rich lipid.

SUMMARY

In order to overcome the problems of low catalytic efficiency, long reaction time and unstable reaction in the process of enzymatic deacidification of long-chain PUFA-rich lipid, the present invention provides a method for enzymatic deacidification by partial glyceride lipase.

It is found during a research that the catalytic function of partial glyceride lipase is also determined by its molecular structure, especially the primary structure. It is found in further research that lipase SMG1 Phe278Asn obtained by mutating Phe at position 278 of Lipase SMG1 to Asn has good deacidification effect and may not catalyze a side reaction of triglyceride in the raw material when used for deacidification of long-chain PUFA-rich lipid, and then the present invention was obtained.

In the present invention, the immobilized Lipase SMG1 Phe278Asn is used as a catalyst for catalyzing the reaction of free fatty acids with short-chain monols to form fatty acid esters in a solvent system, and then the reaction product is separated to obtain a deacidified lipid.

The technical solution of the present invention is as follows:

A partial glyceride lipase is a mutant Lipase SMG1 Phe278Asn obtained by mutating Phe at position 278 of Lipase SMG1 to Asn, and the amino acid sequence thereof is as shown by SEQ ID NO.1.

An enzymatic deacidification method of PUFA-rich lipid comprises the steps of:

1) mixing a PUFA-rich lipid with a non-polar organic solvent and a short-chain monol, and adding immobilized partial glyceride lipase for esterification reaction, the partial glyceride lipase having an amino acid sequence as shown by SEQ ID NO.1;

2) recovering the immobilized enzyme, the organic solvent and the monol to obtain a deacidified PUFA-rich lipid.

In step 1), a mass to volume ratio of the lipid to the organic solvent is 1:(0.4 to 5) g/ml, and a molar ratio of free fatty acids in the lipid to the monol is 1:(1.1 to 4).

In step 1), the partial glyceride lipase is added in an amount of 50 to 200 U/g of the total mass of the reaction substrate.

The temperature of the esterification reaction is 25° C. or less.

In step 1), the immobilized partial glyceride lipase is prepared by immobilization of the partial glyceride lipase and an epoxy resin in a ratio of 10 to 50 mg/g of the resin using the epoxy resin as an immobilization carrier and a phosphate buffer as a buffer.

The immobilization carrier is ECR8285 epoxy resin, the concentration of the buffer is 1.5 moL/L, pH=6.0; and the immobilization time is 7 h.

In step 1), the monol is one or more of methanol, ethanol, and propanol.

The PUFA-rich lipid is one or more of marine fish oil, algae oil or oils rich in polyunsaturated fatty acids having 20 or more carbon atoms.

In step 1), the PUFA-rich lipid has an acid value of 20 to 80 mgKOH/g.

In step 2), the non-polar organic solvent is one or more of n-hexane, n-heptane, and isooctane.

The monol is added in a stepwise manner, wherein ⅓ of the total amount is added at the beginning of the esterification reaction, another ⅓ is added after the reaction is carried out for 6 hours, and the remaining ⅓ is added after the reaction is carried out for 12 hours.

In step 2), the immobilized enzyme is recovered by filtration, and the organic solvent and the monol are recovered by vacuum distillation or molecular distillation (film evaporation). The immobilized partial glyceride lipase Lipase SMG1 Phe278Asn used in the present invention has a significantly higher selectivity for long-chain polyunsaturated fatty acids EPA and DHA than wild-type Lipase SMG1, and the catalytic activity is also significantly improved. Meanwhile, it still maintains high substrate specificity for partial glycerides. The use of the above partial glyceride lipase to catalyze the reaction of free fatty acids in the PUFA-rich lipid with short-chain monols may convert almost all of the free fatty acids into fatty acid esters. The esterification reaction may be carried out at a lower temperature, avoiding the oxidation of PUFA in the lipid.

Studies of the inventors have shown that when the free fatty acids in the PUFA-rich lipid are reacted with the short-chain monols under the presence of the immobilized Lipase SMG1 Phe278Asn, the viscosity of the reaction system is high and the reaction rate becomes slow at a later stage of the reaction. Further studies have shown that when a certain amount of non-polar organic solvent is added to the reaction system, the mass transfer of the reaction and the slow reaction rate at a later stage may be remarkably improved. Therefore, considering the reaction rate and the removal effects of fatty acids, in the reaction of free fatty acids in the PUFA-rich lipid with short-chain monols using immobilized Lipase SMG1 Phe278Asn in the present invention, a certain amount of non-polar organic solvent is added to improve the removal of fatty acids.

Compared with the prior art, the present invention has the following advantages:

(1) in the present invention, the immobilized Lipase SMG1 Phe278Asn is used as a catalyst to avoid the side reaction of triglyceride, which improves the deacidification efficiency of PUFA, and reduces the risk of oxidation of PUFA.

(2) The present invention adopts one or more of n-hexane or isooctane as a solvent and a stepwise method of adding the monol to improve the deacidification efficiency, so that the removal rate of free fatty acids may reach more than 99%, thereby increasing reuse times of the immobilized lipase.

DETAILED DESCRIPTION OF THE EMBODIMENTS

The implementation of the present invention is described in more detail below by way of embodiments. In the embodiments, all percentages are counted by mass.

Preparation of immobilized Lipase SMG1 Phe278Asn: using ECR8285 epoxy resin as an immobilization carrier, partial glyceride lipase is mixed with the ECR8285 epoxy resin in a ratio of 20 mg/g of resin, and a phosphate buffer of 1.5 moL/L and pH=6.0 is used as a buffer with an amount equal to the volume of the enzyme solution; then the mixture is mixed and immobilized at room temperature for 7 hours in a water bath shaker at a rotation speed of 200 rpm. The immobilized enzyme is recovered by filtration through a Buchner funnel and dried under vacuum at 30° C. for 6 h. The immobilized enzyme obtained finally has a protein adsorption amount of 52.7 mg/g, a protein adsorption rate of 82.11%, and an esterase activity of 328 U/g (n-propanol lauric acid method).

Example 1

20 g of decolorized squid oil with an acid value of 26.78 mgKOH/g is added to 0.29 g of anhydrous ethanol (the molar ratio of free fatty acids to the anhydrous ethanol is 3:2) and 80 mL of n-hexane in a 500 mL stoppered Erlenmeyer flask followed by mixing and preheating to 25° C.; then, 80 of the total mass of the reaction substrate of immobilized Lipase SMG1 Phe278Asn is added for esterification at 25° C. with stirring by an air bath shaker at a speed of 200 rpm, and 0.29 g of anhydrous ethanol is subsequently added (the molar ratio of free fatty acids in the squid oil to the total anhydrous ethanol is 1:2 after three times of addition) after reacting for 6 h and 12 h, respectively; then after 30 h of the esterification reaction, the acid value of the squid oil after deacidification is analyzed, wherein the acid value of the squid oil decreases from initially 26.78 mgKOH/g to 0.10 mgKOH/g, the removal rate of free fatty acids reaches 99.63%, and the peroxide value of the recovered deacidified lipid is 3.2 meq/kg (basically the same as the raw material); the immobilized enzyme may be repeatedly used for 6 batches without significant reduction in activity.

Example 2

20 g of decolorized squid oil with an acid value of 26.78 mgKOH/g is added to 0.22 g of anhydrous ethanol (the molar ratio of free fatty acids to the anhydrous ethanol is 2:1) and 60 mL of n-hexane in a 500 mL stoppered Erlenmeyer flask followed by mixing and preheating to 20° C.; then, 100 U/g of the total mass of the reaction substrate of immobilized Lipase SMG1 Phe278Asn is added for esterification at 20° C. with stirring by an air bath shaker at a speed of 200 rpm, and 0.22 g of anhydrous ethanol is subsequently added (the molar ratio of free fatty acids in the squid oil to the total anhydrous ethanol is 2:3 after three times of addition) after reacting for 6 h and 12 h, respectively; then after 30 h of the esterification reaction the acid value of the squid oil after deacidification is analyzed, wherein the acid value of squid oil decreases from initially 26.78 mgKOH/g to 0.19 mgKOH/g, the removal rate of free fatty acids reaches 99.29%, and the peroxide value of the recovered deacidified lipid is 3.1 meq/kg (basically the same as the raw material); the immobilized enzyme may be repeatedly used for 6 batches without significant reduction in activity.

Example 3

20 g of decolorized tuna oil with an acid value of 36.16 mgKOH/g is added to 0.5 g of anhydrous ethanol (the molar ratio of free fatty acids to the anhydrous ethanol is 6:5) and 80 mL of n-hexane in a 500 mL stoppered Erlenmeyer flask followed by mixing and preheating to 25° C.; then, 80 U/g of the total mass of the reaction substrate of immobilized Lipase SMG1 Phe278Asn is added for esterification at 25° C. with stirring by an air bath shaker at a speed of 200 rpm, and 0.5 g of anhydrous ethanol is subsequently added (the molar ratio of free fatty acids in the tuna oil to the total anhydrous ethanol is 2:5 after three times of addition) after reacting for 6 h and 12 h, respectively; then after 30 h of the esterification reaction the acid value of the tuna oil after deacidification is analyzed, wherein the acid value of tuna oil decreases from initially 36.16 mgKOH/g to 0.10 mgKOH/g, the removal rate of free fatty acids reaches 99.72%, and the peroxide value of the recovered deacidified lipid is 2.3 meq/kg (basically the same as the raw material); the immobilized enzyme may be repeatedly used for 6 batches without significant reduction in activity.

Example 4

20 g of decolorized tuna oil with an acid value of 36.16 mgKOH/g is added to 0.28 g of anhydrous methanol (the molar ratio of free fatty acids to the anhydrous methanol is 3:2) and 60 mL of n-hexane in a 500 mL stoppered Erlenmeyer flask followed by mixing and preheating to 20° C.; then, 80 U/g of the total mass of the reaction substrate of immobilized Lipase SMG1 Phe278Asn is added for esterification at 20° C. with stirring by an air bath shaker at a speed of 200 rpm, and 0.28 g of anhydrous methanol is subsequently added (the molar ratio of free fatty acids in the tuna oil to the total anhydrous methanol is 1:2 after three times of addition) after reacting for 6 h and 12 h, respectively; then after 30 h of the esterification reaction the acid value of the tuna oil after deacidification is analyzed, wherein the acid value of tuna oil decreases from initially 36.16 mgKOH/g to 0.14 mgKOH/g, the removal rate of free fatty acids reaches 99.61%, and the peroxide value of the recovered deacidified lipid is 2.2 meq/kg; the immobilized enzyme may be repeatedly used for 6 batches without significant reduction in activity.

Example 5

20 g of decolorized squid oil with an acid value of 26.78 mgKOH/g is added to 0.29 g of anhydrous ethanol (the molar ratio of free fatty acids to the anhydrous ethanol is 3:2) and 80 mL of isooctane in a 500 mL stoppered Erlenmeyer flask followed by mixing and preheating to 25° C.; then, 80 U/g of the total mass of the reaction substrate of immobilized Lipase SMG1 Phe278Asn is added for esterification at 25° C. with stirring by an air bath shaker at a speed of 200 rpm, and 0.29 g of anhydrous ethanol is subsequently added (the molar ratio of free fatty acids in the squid oil to the total anhydrous ethanol is 1:2 after three times of addition) after reacting for 6 h and 12 h, respectively; then after 30 h of the esterification reaction the acid value of the squid oil after deacidification is analyzed, wherein the acid value of squid oil decreases from initially 26.78 mgKOH/g to 0.09 mgKOH/g, the removal rate of free fatty acids reaches 99.66%, and the peroxide value of the recovered deacidified lipid is 3.0 meq/kg (basically the same as the raw material); the immobilized enzyme may be repeatedly used for 6 batches without significant reduction in activity.

Example 6

20 g of decolorized tuna oil with an acid value of 36.16 mgKOH/g is added to 0.5 g of anhydrous ethanol (the molar ratio of free fatty acids to the anhydrous ethanol is 6:5) and 60 mL of isooctane in a 500 mL stoppered Erlenmeyer flask followed by mixing and preheating to 20° C.; then, 80 U/g of the total mass of the reaction substrate of immobilized Lipase SMG1 Phe278Asn is added for esterification at 20° C. with stirring by an air bath shaker at a speed of 200 rpm, and 0.5 g of anhydrous ethanol is subsequently added (the molar ratio of free fatty acids in the tuna oil to the total anhydrous ethanol is 2:5 after three times of addition) after reacting for 6 h and 12 h, respectively; then after 30 h of the esterification reaction the acid value of the tuna oil after deacidification is analyzed, wherein the acid value of tuna oil decreases from initially 36.16 mgKOH/g to 0.11 mgKOH/g, the removal rate of free fatty acids reaches 99.70%, and the peroxide value of the recovered deacidified lipid is 2.2 meq/kg (basically the same as the raw material); the immobilized enzyme may be repeatedly used for 6 batches without significant reduction in activity.

Comparative Example 1

20 g of decolorized squid oil with an acid value of 26.78 mgKOH/g is added to 0.29 g of anhydrous ethanol (the molar ratio of free fatty acids to the anhydrous ethanol is 3:2) and 80 mL of n-hexane in a 500 mL stoppered Erlenmeyer flask followed by mixing and preheating to 25° C.; then, 80 U/g of the total mass of the reaction substrate of immobilized Lipase SMG1 is added for esterification at 25° C. with stirring by an air bath shaker at a speed of 200 rpm, and 0.29 g of anhydrous ethanol is subsequently added (the molar ratio of free fatty acids in the squid oil to the total anhydrous ethanol is 1:2 after three times of addition) after reacting for 6 h and 12 h, respectively; then after 30 h of the esterification reaction the acid value of the squid oil after deacidification is analyzed, wherein the acid value of squid oil decreases from initially 26.78 mgKOH/g to 3.73 mgKOH/g, and the removal rate of free fatty acids reaches 86.07%.

Comparative Example 2

20 g of decolorized squid oil with an acid value of 26.78 mgKOH/g is added to 0.29 g of anhydrous ethanol (the molar ratio of free fatty acids to the anhydrous ethanol is 3:2) and 80 mL of n-hexane in a 500 mL stoppered Erlenmeyer flask followed by mixing and preheating to 25° C.; then, 80 U/g of the total mass of the reaction substrate of immobilized Lipase G "Amano"50 is added for esterification at 25° C. with stirring by an air bath shaker at a speed of 200 rpm, and 0.29 g of anhydrous ethanol is subsequently added (the molar ratio of free fatty acids in the squid oil to the total anhydrous ethanol is 1:2 after three times of addition) after reacting for 6 h and 12 h, respectively; then after 30 h of the esterification reaction the acid value of the squid oil after deacidification is analyzed, wherein the acid value of squid oil decreases from initially 26.78 mgKOH/g to 3.41 mgKOH/g, and the removal rate of free fatty acids reaches 87.27%.

Comparative Example 3

20 g of decolorized tuna oil with an acid value of 36.16 mgKOH/g is added to 0.28 g of anhydrous methanol (the molar ratio of free fatty acids to the anhydrous methanol is 3:2) and 80 mL of isooctane in a 500 mL stoppered Erlenmeyer flask followed by mixing and preheating to 20° C.; then, 80 U/g of the total mass of the reaction substrate of immobilized Lipase SMG1 is added for esterification at 20° C. with stirring by an air bath shaker at a speed of 200 rpm, and 0.28 g of anhydrous methanol is subsequently added (the total molar ratio of free fatty acids to anhydrous methanol in the tuna oil is 1:2 after three times of addition) after reacting for 6 h and 12 h, respectively; then after 30 h of the esterification reaction the acid value of the tuna oil after deacidification is analyzed, wherein the acid value of tuna oil decreases from initially 36.16 mgKOH/g to 4.89 mgKOH/g, and the removal rate of free fatty acids reaches 86.48%.

Comparative Example 4

20 g of decolorized tuna oil with an acid value of 36.16 mgKOH/g is added to 0.5 g of anhydrous ethanol (the molar ratio of free fatty acids to the anhydrous ethanol is 6:5) and 80 mL of n-hexane in a 500 mL stoppered Erlenmeyer flask followed by mixing and preheating to 25° C.; then, 80 U/g of the total mass of the reaction substrate of immobilized Lipase SMG1 is added for esterification at 25° C. with stirring by an air bath shaker at a speed of 200 rpm, and 0.5 g of anhydrous ethanol is subsequently added (the molar ratio of free fatty acids in the tuna oil to the total anhydrous ethanol is 2:5 after three times of addition) after reacting for 6 h and 12 h, respectively; then after 30 h of the esterification reaction the acid value of the tuna oil after deacidification is analyzed, wherein the acid value of tuna oil decreases from initially 36.16 mgKOH/g to 5.69 mgKOH/g, and the removal rate of free fatty acids reaches 84.26%.

Comparative Example 5

20 g of decolorized tuna oil with an acid value of 36.16 mgKOH/g is added to 0.4 g of anhydrous ethanol (the molar ratio of free fatty acids to the anhydrous ethanol is 3:2) and 80 mL of isooctane in a 500 mL stoppered Erlenmeyer flask followed by mixing and preheating to 25° C.; then, 80 U/g of the total mass of the reaction substrate of immobilized Lipase SMG1 is added for esterification at 25° C. with stirring by an air bath shaker at a speed of 200 rpm, and 0.4 g of anhydrous ethanol is subsequently added (the molar ratio of free fatty acids in the tuna oil to the total anhydrous ethanol is 1:2 after three times of addition) after reacting for 6 h and 12 h, respectively; then after 30 h of the esterification reaction the acid value of the tuna oil after deacidification is analyzed, wherein the acid value of tuna oil decreases from initially 36.16 mgKOH/g to 5.39 mgKOH/g, and the removal rate of free fatty acids reaches 85.09%.

Comparative Example 6

20 g of decolorized squid oil with an acid value of 26.78 mgKOH/g is added to 0.87 g of anhydrous ethanol (the total molar ratio of free fatty acids to the anhydrous ethanol is 1:2) and 80 mL of n-hexane in a 500 mL stoppered Erlenmeyer flask followed by mixing and preheating to 25° C.; then, 80 U/g of the total mass of the reaction substrate of immobilized Lipase SMG1 Phe278Asn is added for esterification at 25° C. with stirring by an air bath shaker at a speed of 200 rpm; and then, after esterification for 30 h, the acid value of the squid oil after deacidification is analyzed, wherein the acid value of squid oil decreases from initially 26.78 mgKOH/g to 1.70 mgKOH/g, and the removal rate of free fatty acids reaches 93.65%.

Comparative Example 7

20 g of decolorized squid oil with an acid value of 26.78 mgKOH/g is added to 0.29 g of anhydrous ethanol (the molar ratio of free fatty acids to the anhydrous ethanol is 3:2) in a 100 mL stoppered Erlenmeyer flask followed by mixing and preheating to 25° C.; then, 80 U/g of the total mass of the reaction substrate of immobilized Lipase SMG1 Phe278Asn is added for esterification at 25 CC with stirring by an air bath shaker at a speed of 200 rpm, and 0.29 g of anhydrous ethanol is subsequently added (the molar ratio of free fatty acids in the squid oil to the total anhydrous ethanol is 1:2 after three times of addition) after reacting for 6 h and 12 h, respectively; then after 30 h of the esterification reaction the acid value of the squid oil after deacidification is analyzed, wherein the acid value of squid oil decreases from initially 26.78 mgKOH/g to 1.14 mgKOH/g, and the removal rate of free fatty acids reaches 95.74%. After the immobilized enzyme is used repeatedly for 3 batches, its activity remains 48% of the initial activity.

What is claimed is:

1. An enzymatic deacidification method for polyunsaturated fatty acid (PUFA)-rich oil comprising the steps of:
   1) mixing the PUFA-rich oil with a non-polar organic solvent and a short-chain monol, and adding immobilized partial glyceride lipase for esterification reaction to remove free fatty acids in the PUFA-rich oil, the monol is added in a stepwise manner, wherein ⅓ of the total amount is added at the beginning of the esterification reaction, another ⅓ is added after the reaction is carried out for 6 hours, and the remaining ⅓ is added after the reaction is carried out for 12 hours;
   wherein the monol is one or more of methanol, ethanol, and propanol, the PUFA-rich oil is one or more of marine fish oil, algae oil or oils rich in polyunsaturated fatty acids having 20 or more carbon atoms, the PUFA-rich oil has an acid value of 20 to 80 mgKOH/g, and the partial glyceride lipase is a mutant Lipase SMG1 Phe278Asn obtained by mutating Phe at position 278 of Lipase SMG1 to Asn, the partial glyceride lipase comprises an entire amino acid sequence of SEQ ID NO:1; and
   2) recovering the immobilized enzyme, the organic solvent and the monol to obtain a deacidified PUFA-rich oil.

2. The method according to claim 1, wherein in step 1), a mass to volume ratio of the oil to the organic solvent is 1: (0.4 to 5) g/ml, and a molar ratio of free fatty acids in the oil to the monol is 1: (1.1 to 4).

3. The method according to claim 1, wherein in step 1), the partial glyceride lipase is added in an amount of 50 to 200 U/g of the total mass of the reaction substrate, and the temperature of the esterification reaction is 25° C. or less.

4. The method according to claim 1, wherein in step 1), the immobilized partial glyceride lipase is prepared by immobilization of the partial glyceride lipase and an epoxy resin in a ratio of 10 to 50 mg/g of the resin using the epoxy resin as an immobilization carrier and a phosphate buffer as a buffer.

5. The method according to claim 1, wherein in step 2), the non-polar organic solvent is one or more of n-hexane, n-heptane, and isooctane.

6. The preparation method according to claim 1, wherein in step 2), the immobilized enzyme is recovered by filtration, and the organic solvent and the monol are recovered by vacuum distillation or molecular distillation.

* * * * *

SEQUENCE LISTING

```
<160> NUMBER OF SEQ ID NOS: 1

<210> SEQ ID NO 1
<211> LENGTH: 279
<212> TYPE: PRT
<213> ORGANISM: Artificial Sequence
<220> FEATURE:
<223> OTHER INFORMATION: Synthetic peptide
```

```
<400> SEQUENCE: 1

Gly Arg Gly Gly Ser Ser Thr Asp Gln Pro Val Ala Asn Pro Tyr Asn
1               5                   10                  15

Thr Lys Glu Ile Ser Leu Ala Ala Gly Leu Val Gln Gln Thr Tyr Cys
            20                  25                  30

Asp Ser Thr Glu Asn Gly Leu Lys Ile Gly Asp Ser Glu Leu Leu Tyr
        35                  40                  45

Thr Met Gly Glu Gly Tyr Ala Arg Gln Arg Val Asn Ile Tyr His Ser
    50                  55                  60

Pro Ser Leu Gly Ile Ala Val Ala Ile Glu Gly Thr Asn Leu Phe Ser
65              70                  75                  80

Leu Asn Ser Asp Leu His Asp Ala Lys Phe Trp Gln Glu Asp Pro Asn
            85                  90                  95

Glu Arg Tyr Ile Gln Tyr Tyr Pro Lys Gly Thr Lys Leu Met His Gly
            100                 105                 110

Phe Gln Gln Ala Tyr Asn Asp Leu Met Asp Asp Ile Phe Thr Ala Val
            115                 120                 125

Lys Lys Tyr Lys Lys Glu Lys Asn Glu Lys Arg Val Thr Val Ile Gly
130             135                 140

His Ser Leu Gly Ala Ala Met Gly Leu Leu Cys Ala Met Asp Ile Glu
145                 150                 155                 160

Leu Arg Met Asp Gly Gly Leu Tyr Lys Thr Tyr Leu Phe Gly Leu Pro
                165                 170                 175

Arg Leu Gly Asn Pro Thr Phe Ala Ser Phe Val Asp Gln Lys Ile Gly
            180                 185                 190

Asp Lys Phe His Ser Ile Ile Asn Gly Arg Asp Trp Val Pro Thr Val
        195                 200                 205

Pro Pro Arg Ala Leu Gly Tyr Gln His Pro Ser Asp Tyr Val Trp Ile
    210                 215                 220

Tyr Pro Gly Asn Ser Thr Ser Ala Lys Leu Tyr Pro Gly Gln Glu Asn
225                 230                 235                 240

Val His Gly Ile Leu Thr Val Ala Arg Glu Phe Asn Asn Asp Asp His
                245                 250                 255

Gln Gly Ile Tyr Phe His Thr Gln Ile Gly Ala Val Met Gly Glu Cys
            260                 265                 270

Pro Ala Gln Val Gly Asn His
            275
```